United States Patent [19]

Kuroki et al.

[11] Patent Number: 5,798,344
[45] Date of Patent: Aug. 25, 1998

[54] PHOSPHONIC ESTER DERIVATIVES OF QUINAZOLINONES

[75] Inventors: Yasuhisa Kuroki; Kazuyoshi Miyata; Yoshihiko Tsuda; Yasuhide Inoue, all of Naruto; Jun Kanaya; Keigo Sato, both of Tokushima-ken, all of Japan

[73] Assignee: Otsuka Pharmaceutical Factory, Inc., Tokushima, Japan

[21] Appl. No.: 704,740

[22] PCT Filed: Feb. 27, 1995

[86] PCT No.: PCT/JP95/00303

§ 371 Date: Sep. 5, 1996

§ 102(e) Date: Sep. 5, 1996

[87] PCT Pub. No.: WO95/24410

PCT Pub. Date: Sep. 14, 1995

[30] Foreign Application Priority Data

Mar. 8, 1994 [JP] Japan ................ 6-037361
Jun. 8, 1994 [JP] Japan ................ 6-126526
Sep. 19, 1994 [JP] Japan ................ 6-251484

[51] Int. Cl.$^6$ ............... A61K 31/675; C07F 9/6512
[52] U.S. Cl. ............... 514/80; 544/243; 544/244
[58] Field of Search ............... 544/243, 244; 514/80

[56] References Cited

U.S. PATENT DOCUMENTS 5,624,918 4/1997 Kuroki et al. ............... 544/244

FOREIGN PATENT DOCUMENTS

0655456A1 1/1995 European Pat. Off. .
9112001 8/1991 WIPO .
WO9112001 8/1991 WIPO .
9500524 1/1995 WIPO .

OTHER PUBLICATIONS

Chemical Abstract, "Preparation of quinolines as hypolipemics and antidiabetics" vol. 119: 95360, Aug. 30, 1993.

*Primary Examiner*—Mukund J. Shah
*Assistant Examiner*—Pavanaram K. Sripada
*Attorney, Agent, or Firm*—Sughrue, Mion, Zinn, Macpeak & Seas, PLLC

[57] ABSTRACT

The invention provides a phosphonic diester derivative of the formula:

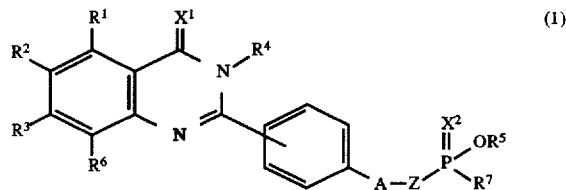

wherein $R^1$-$R^7$ are substituent groups, as defined in the specification.

The derivatives according to the invention are useful as therapeutic or preventive compositions for hyperlipidemia, hypertension, and diabetes.

17 Claims, No Drawings

PHOSPHONIC ESTER DERIVATIVES OF QUINAZOLINONES

TECHNICAL FIELD

This application is a 371 of PCT/JP95/00303, F.D. Feb. 27, 1995.

The present invention relates to novel phosphonic ester derivatives.

PRIOR ART

The phosphonic ester derivatives of the invention are novel compounds not heretofore described in the literature.

The object of the invention is to provide compounds of value as medicines as will be described hereinafter.

DISCLOSURE OF THE INVENTION

The present invention provides a phosphonic ester derivative of the following formula (1):

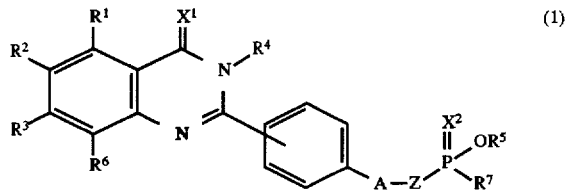

wherein $R^1$, $R^2$, $R^3$ and $R^6$ are the same or different and each represents a hydrogen atom, a lower alkyl group, a halogen atom, a nitro group, a lower alkoxy group, a cyano group, a phenylsulfonylamino group, a benzoylamino group, an amino group or a halogen-substituted lower alkyl group, $R^4$ represents a phenyl group, a lower alkyl group, a phenyl (lower)alkyl group optionally substituted by halogen on the phenyl ring, a lower alkenyl group, a carboxy(lower)alkyl group, a (lower)alkoxycarbonyl(lower)alkyl group, a (lower)alkoxy(lower)alkyl group, a lower alkynyl group, a benzoyl(lower)alkyl group, an amino group, a di(lower) alkanoylamino group, a benzylideneamino group optionally having lower alkoxy on the phenyl ring or a pyridylmethylideneamino group, $R^5$ represents a lower alkyl group, $R^7$ represents a lower alkoxy group, a hydroxyl group, a phenyl group, a phenyl(lower)alkoxy group optionally having halogen on the phenyl ring or a phenyl(lower)alkylamino group, $X^1$ and $X^2$ independently represent an oxygen atom or a sulfur atom, A represents an oxygen atom or a single bond, and Z represents a lower alkylene group.

Each of the groups relevant to the above formula (1) includes the following exemplary species.

The halogen atom includes fluorine, chlorine, bromine and iodine.

The lower alkoxy group includes methoxy, ethoxy, propoxy, isopropoxy, butoxy, tert-butoxy, pentyloxy, hexyloxy and so on.

The lower alkyl group includes methyl, ethyl, propyl, isopropyl, butyl, tert-butyl, pentyl, hexyl and so on.

The phenyl(lower)alkyl group optionally substituted by halogen on the phenyl ring includes benzyl, α-phenethyl, β-phenethyl, 1-phenylpropyl, 2-phenylpropyl, 3-phenylpropyl, 4-phenylbutyl, 5-phenylpentyl, 6-phenylhexyl, 2-bromobenzyl, 3-bromobenzyl, 4-bromobenzyl, 4-chlorobenzyl, 4-fluorobenzyl, 4-iodobenzyl, 2-bromo-4-fluorobenzyl, 2-fluoro-4-bromobenzyl, 2-chloro-4-fluorobenzyl, 2-fluoro-4-chlorobenzyl, 2-bromo-4-chlorobenzyl, 2-chloro-4-bromobenzyl, 2-iodo-4-bromobenzyl, 3-chloro-5-bromobenzyl, 3-bromo-5-fluorobenzyl, 3-chloro-5-fluorobenzyl, 3-iodo-5-bromobenzyl, 3-chloro-5-iodobenzyl and so on.

The lower alkenyl group includes vinyl, 1-methylvinyl, 1-propenyl, 2-propenyl, 1-butenyl, 2-butenyl, 3-butenyl, 2,2-dimethylvinyl, 1-pentenyl, 2-pentenyl, 3-pentenyl, 4-pentenyl, 1-hexenyl, 2-hexenyl, 3-hexenyl, 4-hexenyl, 5-hexenyl and so on.

The carboxy(lower)alkyl group includes carboxymethyl, 1-carboxyethyl, 2-carboxyethyl, 1-carboxypropyl, 2-carboxypropyl, 3-carboxypropyl, 4-carboxybutyl, 5-carboxypentyl, 6-carboxyhexyl and so on.

The (lower)alkoxycarbonyl(lower)alkyl group includes methoxycarbonylmethyl, ethoxycarbonylmethyl, propoxycarbonylmethyl, isopropoxycarbonylmethyl, butoxycarbonylmethyl, tert-butoxycarbonylmethyl, pentyloxycarbonylmethyl, hexyloxycarbonylmethyl, 1-methoxycarbonylethyl, 2-methoxycarbonylethyl, 1-ethoxycarbonylethyl, 2-ethoxycarbonylethyl, 3-methoxycarbonylpropyl, 3-ethoxycarbonylpropyl, 4-ethoxycarbonylbutyl, 5-ethoxycarbonylpentyl, 6-ethoxycarbonylhexyl and so on.

The halogen-substituted lower alkyl group includes trifluoromethyl, pentafluoroethyl, heptafluoropropyl, nonafluorobutyl, undecafluoropentyl, tridecafluorohexyl and so on.

The (lower)alkoxy(lower)alkyl group includes methoxymethyl, ethoxymethyl, propoxymethyl, butoxymethyl, pentyloxymethyl, hexyloxymethyl, 2-methoxyethyl, 3-methoxypropyl, 4-methoxybutyl, 5-methoxypentyl, 6-methoxyhexyl and so on.

The lower alkynyl group includes ethynyl, 2-propynyl, 3-butynyl, 4-pentynyl, 5-hexynyl and so on.

The benzoyl(lower)alkyl group includes benzoylmethyl, 2-benzoylethyl, 3-benzoylpropyl, 4-benzoylbutyl, 5-benzoylpentyl, 6-benzoylhexyl and so on.

The di(lower)alkanoylamino group includes diacetylamino, dipropionylamino, dibutylylamino, divalerylamino, dihexanoylamino, diheptanoylamino and so on.

The benzylideneamino group optionally having lower alkoxy on the phenyl ring includes unsubstituted benzylideneamino, 4-methoxybenzylideneamino, 3-methoxybenzylideneamino, 2-methoxybenzylideneamino, 4-ethoxybenzylideneamino, 4-propoxybenzylideneamino and so on.

The pyridylmethylideneamino group includes 2-pyridylmethylideneamino, 3-pyridylmethylideneamino, 4-pyridylmethylideneamino and so on.

The phenyl(lower)alkoxy group optionally having halogen on the phenyl ring includes benzyloxy, 2-phenylethoxy, 3-phenylpropoxy, 4-penylbutoxy, 5-phenylpentyloxy, 6-phenylhexyloxy, 4-chlorobenzyloxy, 3-chlorobenzyloxy, 2-chlorobenzyloxy, 4-bromobenzyloxy and so on.

The phenyl(lower)alkylamino group includes benzylamino, 2-phenylethylamino, 3-phenylpropylamino, 4-phenylbutylamino, 5-phenylpentylamino, 6-phenylhexylamino and so on.

The lower alkylene group includes methylene, ethylene, trimethylene, tetramethylene, pentamethylene, hexamethylene and so on.

The phosphonic ester derivative of the formula (1) of the invention has excellent hypolipidemic, vasodepressor and hypoglycemic activities and is useful as therapeutic agents for hyperlipidemia, hypertension and diabetes. More specifically, the derivative can treat or prevent various types of hyperlipidemic diseases such as hypercholesterolemia, hypertriglyceridemia, hyperinsulinemia, hyperphospholipidemia and hyper-free fatty acidemia, hypertension and diabetes.

Examples of the derivatives of the formula (1) of the invention include compounds wherein $R^1$, $R^2$, $R^3$ and $R^6$ are the same or different and each represents a hydrogen atom, a halogen atom, a nitro group, a lower alkoxy group or a halogen-substituted lower alkyl group, $R^4$ represents a phenyl group, a lower alkyl group, a phenyl(lower)alkyl group optionally substituted by halogen on the phenyl ring, a lower alkenyl group, a carboxy(lower)alkyl group or a (lower)alkoxycarbonyl(lower)alkyl group, $R^5$ represents a lower alkyl group, $R^7$ represents the same group as $OR^5$, A represents a single bond, Z represents a methylene group, and $X^1$ and $X^2$ independently represent an oxygen atom or a sulfur atom.

Typical examples of the derivatives of the invention particularly useful as medicine to treat or prevent diabetes and hyperlipidemia include those represented by the following formula (1').

Formula (1'):

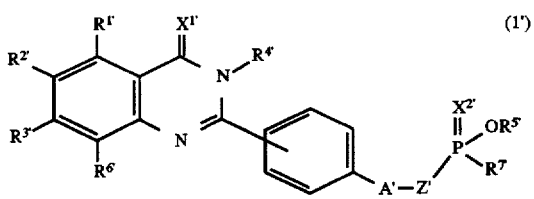

wherein $R^{1'}$ represents a hydrogen atom or a halogen atom, $R^{2'}$ represents a hydrogen atom, a lower alkyl group, a halogen atom, a nitro group or a lower alkoxy group, $R^{3'}$ represents a hydrogen atom, a halogen atom, a nitro group, a halogen-substituted lower alkyl group, a cyano group, a phenylsulfonylamino group, a benzoylamino group, an amino group or a lower alkoxy group, $R^{4'}$ represents a phenyl group, a lower alkyl group, a phenyl(lower)alkyl group optionally substituted by halogen on the phenyl ring, a lower alkenyl group, a carboxy(lower)alkyl group, a (lower)alkoxy-carbonyl(lower)alkyl group, a (lower)alkoxy (lower)alkyl group, a lower alkynyl group, a benzoyl(lower)alkyl group, an amino group, a di(lower)alkanoylamino group, a benzylideneamino group optionally substituted by lower alkoxy on the phenyl ring or a pyridylmethylideneamino group, $R^{5'}$ represents a lower alkyl group, $R^{6'}$ represents a hydrogen atom, a lower alkoxy group or a halogen atom, $R^{7'}$ represents a lower alkoxy group, a hydroxyl group, a phenyl group, a phenyl(lower)alkoxy group optionally having halogen on he phenyl ring or a phenyl(lower)alkylamino group, $X^{1'}$ and $X^{2'}$ independently represent an oxygen atom or a sulfur atom, A' represents an oxygen atom or a single bond, Z' represents an ethylene group when A' represents an oxygen atom, and Z' represents a methylene group when A' represents a single bond.

The derivatives of the following formula (1") are particularly preferable among those represented by the above formula (1').

Formula (1"):

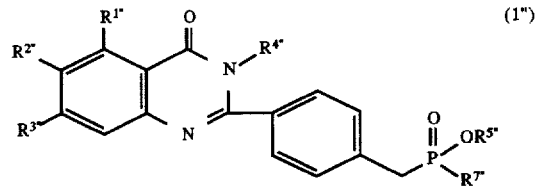

wherein $R^{1''}$ represents a hydrogen atom or a halogen atom, $R^{2''}$ represents a hydrogen atom, a halogen atom, a nitro group, a lower alkyl group or a lower alkoxy group, $R^{3''}$ represents a hydrogen atom, a halogen atom, a halogen-substituted lower alkyl group or a lower alkoxy group, $R^{4''}$ represents a lower alkyl group, a phenyl(lower)alkyl group, a lower alkynyl group, a pyridylmethylidneamino group or a lower alkenyl group, $R^{5''}$ represents a lower alkyl group, and $R^{7''}$ represents a lower alkoxy group, a phenyl group or a phenyl(lower)alkylamino group.

Preferred derivatives of the formula (1") are as follows:

(a) a derivative wherein $R^{1''}$ represents a hydrogen atom, $R^{2''}$ represents a halogen atom, a nitro atom or a lower alkoxy group, $R^{3''}$ represents a hydrogen atom or a lower alkoxy group, $R^{4''}$ represents a lower alkyl group, a phenyl(lower)alkyl group or a lower alkenyl group, and $R^{7''}$ represents a lower alkoxy group;

(b) a derivative wherein $R^{2''}$ represents a hydrogen atom or a lower alkyl group, $R^{3''}$ represents a hydrogen atom, a halogen-substituted lower alkyl group or a halogen atom, and $R^{4''}$ represents a lower alkyl group, a phenyl (lower)alkyl group, a lower alkynyl group or a pyridylmethylideneamino group;

(c) a derivative as defined above in (b) wherein $R^{2''}$ represents a hydrogen atom and $R^{3''}$ represents a hydrogen atom or a halogen atom; and (d) a derivative as defined above in (c) wherein $R^{1''}$ represents a hydrogen atom, $R^{3''}$ represents a halogen atom, and $R^{7''}$ represents a lower alkoxy group or a phenyl(lower)alkylamino group.

The derivative as defined above in (a) is particularly suitable as the active ingredient of therapeutic or preventive agents for hyperlipidemia. The derivatives defined in (b)–(d) are particularly suitable as the active ingredient of therapeutic or preventive agents for diabetes.

Some of the most suitable derivatives of the invention are diethyl 4-(7-chloro-3-methyl-4(3H)-quinazolinon-2-yl) benzylphosphonate, diethyl 4-(7-bromo-3-methyl-4(3H)-quinazolinon-2-yl)benzylphosphonate and ethyl P-[4-(7-chloro-3-methyl-4(3H)-quinazolinon-2-yl)benzyl]-N-benzylphosphonamidate. Among them diethyl 4-(7-chloro-3-methyl-4(3H)-quinazolinon-2-yl)benzylphosphonate is the most suitable.

The phosphonic ester derivative of the formula (1) of the invention can be prepared by various processes. Specific examples of useful processes will be given below in Reaction schemes.

[Reaction scheme-1]

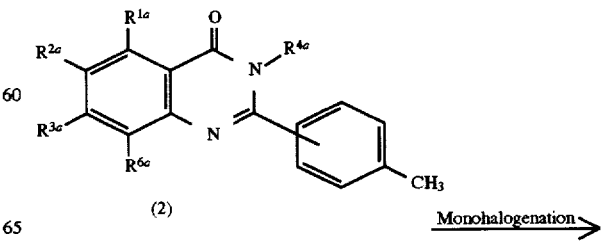

(2)

Monohalogenation⟶

-continued

[Reaction scheme-1]

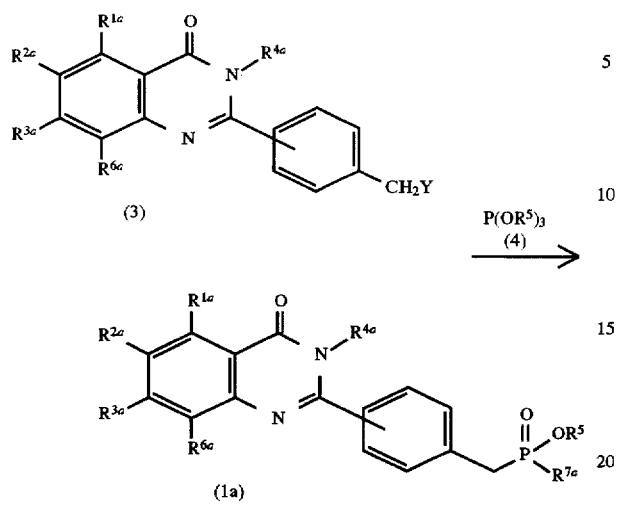

(3)

P(OR⁵)₃ (4)

(1a)

wherein $R^5$ is as defined above, $R^{1a}$, $R^{2a}$, $R^{3a}$ and $R^{6a}$ are the same or different and each represents a hydrogen atom, a halogen atom, a nitro group, a lower alkoxy group, a cyano group or a halogen-substituted lower alkyl group, $R^{4a}$ represents a phenyl group, a lower alkyl group, a phenyl(lower) alkyl group optionally substituted by halogen on the phenyl ring, a lower alkenyl group, a carboxy(lower)alkyl group, a (lower)alkoxycarbonyl(lower)alkyl group, a lower alkynyl group, a (lower)alkoxy(lower)alkyl group or a benzoyl (lower)alkyl group, Y represents a halogen atom and $R^{7a}$ represents the same group as $OR^5$.

In Reaction scheme-1, the monohalogenation reaction of the 2-(tolyl)-4(3H)-quinazolinone derivative (2) can be carried out using a halogenating agent such as N-bromosuccinimide (NBS), N-chlorosuccinimide (NCS) or bromine in the presence of a catalyst such as benzoyl peroxide, α,α'-azobisisobutyronitrile (AIBN) or tert-butylhydroperoxide in an inert solvent such as benzene or carbon tetrachloride. The halogenating agent is usually used in an amount of about 1 to 1.1 moles per mole of the compound (2). The reaction usually goes to completion at about 50° C. to the reflux temperature of the solvent in about 1–20 hours.

The reaction between the resulting benzyl halide derivative (3) and trialkyl phosphite (4) is preferably carried out without using any solvent, or may be carried out in a solvent which does not adversely affect the reaction, such as a lower alcohol, an aromatic or aliphatic hydrocarbon or N,N-dimethylformamide (DMF). The trialkyl phosphite (4) is preferably used in an amount of about 1 to 10 moles per mole of the compound (3). The reaction temperature is preferably about 130°–180° C. The reaction time is usually about 0.5–3 hours, although it may vary depending on the benzyl halide derivative (3) used.

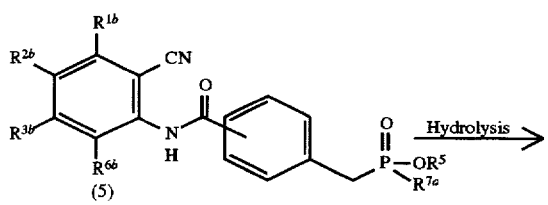

(5)

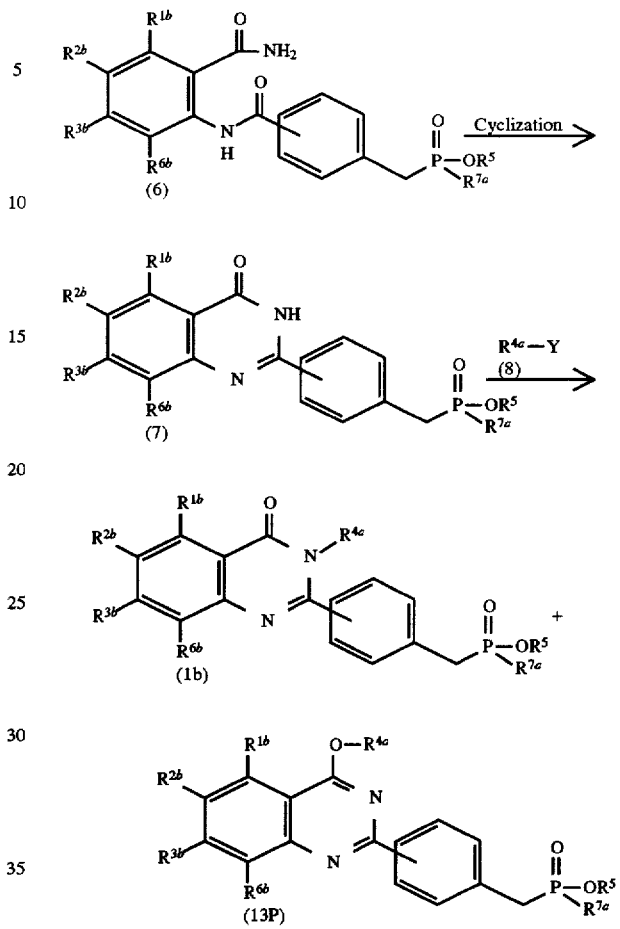

wherein $R^{4a}$, $R^5$, $R^{7a}$ and Y are as defined hereinabove; $R^{1b}$, $R^{2b}$, $R^{3b}$ and $R^{6b}$ are the same or different and each represents a hydrogen atom, a lower alkyl group, a halogen atom, a nitro group, a lower alkoxy group, a cyano group or a halogen-substituted lower alkyl group.

In Reaction scheme-2, the hydrolysis reaction of the nitrile compound (5) can be carried out using an aqueous solution of about 10–30% hydrogen peroxide in the presence of a base catalyst such as sodium hydroxide or potassium hydroxide without using any solvent or in an inert solvent such as tetrahydrofuran (THF), methanol or 1,4-dioxane. The aqueous solution of hydrogen peroxide is usually used in an amount of about 1 to 10 moles per mole of the compound (5). The base catalyst is usually used in an equimolar to small excess proportion relative to the compound (5). The reaction usually goes to completion at room temperature to the reflux temperature of the solvent in about 2–20 hours.

The cyclization reaction of the carbamoyl derivative (6) thus obtained can be carried out using an aqueous solution of about 1–6N alkali such as sodium hydroxide or potassium hydroxide in an inert solvent such as a lower alcohol or 1,4-dioxane. The alkali is usually used in an equimolar to small excess proportion relative to the compound (6). The reaction can be carried out at room temperature to the reflux temperature of the solvent for about 1–10 hours.

The reaction between the cyclic compound (7) and alkyl halide derivative (8) can be carried out in the presence of a base such as metallic sodium, sodium hydride or potassium tert-butoxide in the presence of an inert solvent such as THF, a lower alcohol, 1,4-dioxane or DMF. The base is usually used in an equimolar to small excess proportion relative to the compound (7). The reaction temperature is preferably about 0°–60° C. The reaction usually goes to completion in about 0.5–10 hours, giving the compound (1b) of the invention.

According to the above process, the compound (13P) might be obtained as a byproduct.

The starting compound (5) in the above Reaction scheme-2 can be obtained according to the method described in U.S. Pat. No. 4,822,780.

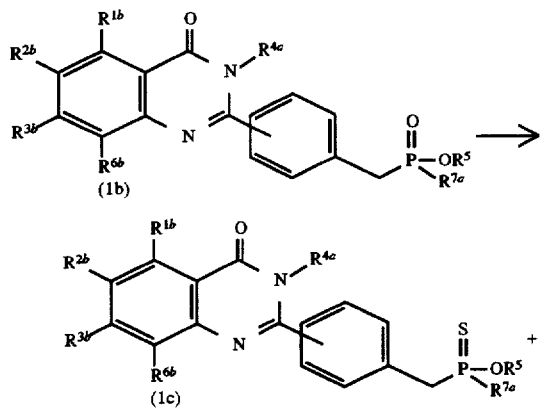

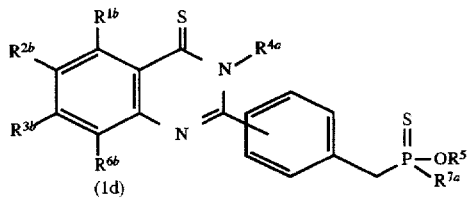

wherein $R^{1b}$, $R^{2b}$, $R^{3b}$, $R^{4a}$, $R^5$, $R^{6b}$ and $R^{7a}$ are the same as defined hereinabove.

As shown in Reaction scheme-3, the compound (1b) of the invention can be converted into compounds (1c) and (1d) by treating the compound (1b) with a sulfur-containing reagent such as the Lawesson's Reagent [2,4-bis(4-methoxyphenyl)-1,3-dithia-2,4-diphosphetane-2,4-disulfide] or phosphorus pentasulfide. This conversion treatment can be carried out in an inert solvent such as benzene, toluene, xylene or acetonitrile using about 2 equivalents of the sulfur-containing reagent relative to the compound (1b) at the reflux temperature of the solvent for about 2–10 hours.

According to the above process, the compounds (1c) and (1d) are obtained as a mixture. These compounds can be easily separated by conventional separation and purification methods as will be mentioned later.

[Reaction scheme-4]

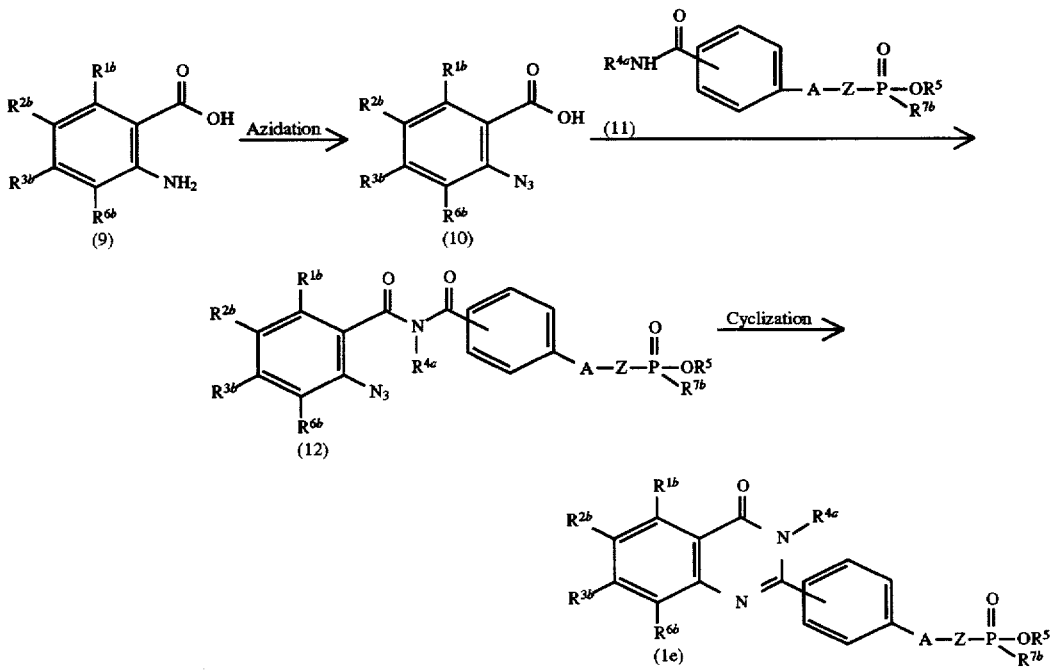

wherein $R^{1b}$, $R^{2b}$, $R^{3b}$, $R^{4a}$, $R^5$, $R^{6b}$, A and Z are as defined hereinabove and $R^{7b}$ represents a lower alkoxy group, a phenyl group or a phenyl(lower)alkoxy group optionally substituted by halogen on the phenyl ring.

In Reaction scheme-4, the azidation reaction of the 2-aminobenzoic acid derivative (9) can be carried out by reacting the derivative (9) with a nitrite such as sodium nitrite or potassium nitrite in an amount of about 1–1.2 moles per mole of the derivative (9) in an aqueous solution of about 2–6N acid such as hydrochloric acid or hydrobromic acid, and then reacting the reaction product with an azide such as sodium azide or potassium azide in an amount of about 1–1.1 moles per mole of the reaction product. These reactions usually go to completion at about 0° C. to room temperature in about 10 to 20 minutes respectively.

The azide derivative (10) thus obtained is reacted with a chlorinating agent such as thionyl chloride or oxalyl chloride in a solvent such as an aromatic or aliphatic hydrocarbon or DMF, or preferably without using any solvent. The acid chloride thus obtained is reacted with a benzylphosphonic acid derivative (11) to give an imide derivative (12).

The reaction for producing the acid chloride can be carried out using about 1 to 10 moles of a chlorinating agent per mole of the compound (10) at about 50° C. to the reflux temperature of the solvent. The reaction time is preferably about 1–2 hours, although it may vary depending on the chlorinating agent used. The reaction between the acid chloride and the compound (11) can be carried out in the presence of a base such as triethylamine, pyridine or 4-dimethylaminopyridine in an inert solvent such as benzene, xylene or carbon tetrachloride. The compound (11) and the base are used in an amount of about 1 to 1.2 moles per mole of the compound (10), respectively. The reaction temperature is preferably room temperature to the reflux temperature of the solvent, and the reaction time is usually about 2–20 hours.

The cyclization reaction of the imide derivative (12) obtained above can be carried out in the presence of trialkyl or triarylphosphine under an inert atmosphere and in a solvent which does not adversely affect the reaction, such as an aromatic or aliphatic hydrocarbon. The amount of trialkyl or triarylphosphine to be used is preferably about 1 to 1.1 mole per mole of the compound (12), and the reaction temperature is preferably about 0° C. to room temperature. The reaction generally goes to completion in about 0.5 to 3 hours.

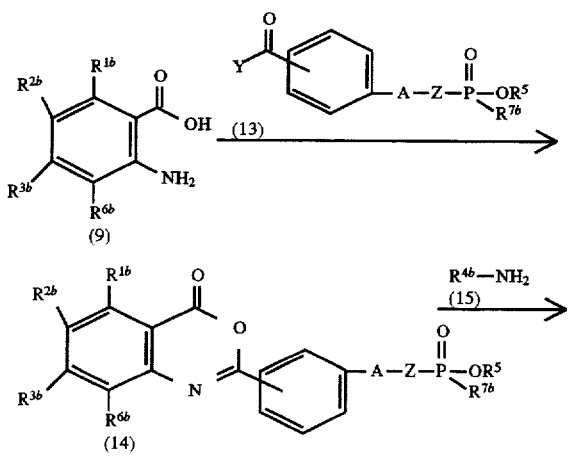

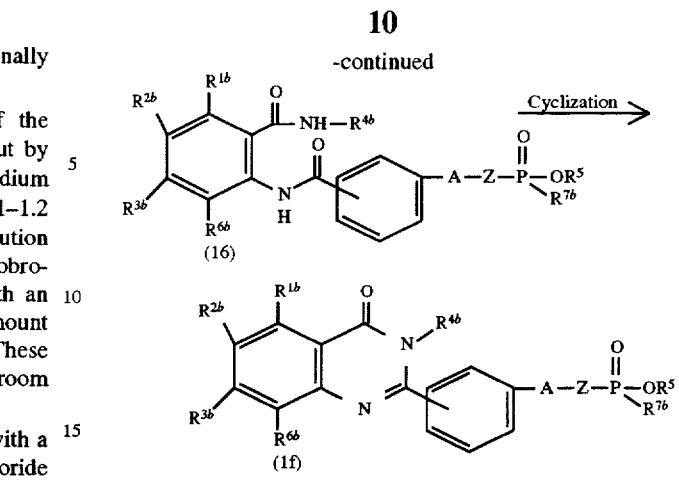

wherein $R^{1b}$, $R^{2b}$, $R^{3b}$, $R^5$, $R^{6b}$, $R^{7b}$, A, Y and Z are as defined above, $R^{4b}$ represents a phenyl group, a lower alkyl group, a phenyl(lower)alkyl group optionally substituted by halogen on the phenyl ring, a lower alkenyl group, a (lower)alkoxycarbonyl(lower)alkyl group, a (lower)alkoxy (lower)alkyl group, a (lower)alkynyl group or a benzoyl (lower)alkyl group.

In Reaction scheme-5, the reaction between the 2-aminobenzoic acid derivative (9) and acid halide (13) can ben carried out in the presence of an acid acceptor in an inert solvent. Examples of useful inert solvents include aromatic or aliphatic hydrocarbons such as benzene, toluene, xylene and petroleum ether, ethers such as diethyl ether, ketones such as acetone, methyl ethyl ketone and acetophenone, and halogenated hydrocarbons such as dichloromethane, chloroform, carbon tetrachloride and 1,2-dichloroethane. Examples of preferable acid acceptors (bases) are amines such as triethylamine, N,N-diethylaniline, N-methylmorpholine, pyridine and 4-dimethylaminopyridine. The reaction is usually carried out at about 0° C. to room temperature for about 0.5–10 hours. If necessary, after an ester of haloformic acid such as methyl chloroformate or ethyl chloroformate and an acid anhydride such as acetic anhydride or propionic anhydride or thionyl chloride are added to the reaction system, a supplemental reaction may be carried out in the presence of the above-mentioned acid acceptor (base) at about 0° C. to room temperature for about 0.5–10 hours. When the supplemental reaction is carried out, acid halide (13) is preferably used in an equimolar to small excess proportion relative to the 2-aminobenzoic acid derivative (9). When no supplemental reaction is carried out, the acid halide (13) is preferably used in an amount of about 2 to 2.2 moles per mole of the derivative (9). In any case, the acid acceptor is preferably used in an amount of 2 moles to an excess per mole of the 2-aminobenzoic acid derivative (9).

The compound (14) thus obtained is converted into the compound (16) by reacting the compound (14) with an amine (15) in an amount of 1 mole to an excess per mole of the compound (14). The reaction can be carried out without using any solvent or in an inert solvent such as THF, methanol or 1,4-dioxane at about 0° C. to room temperature for 0.5–10 hours.

The compound (1f) of the invention can be obtained by cyclizing the compound (16) thus obtained. The cyclization reaction can be carried out in an inert solvent in the presence of a silicon compound and a base. Examples of useful inert solvents include aromatic or aliphatic hydrocarbons such as benzene, toluene, xylene and petroleum ether, ethers such as diethyl ether, and halogenated hydrocarbons such as dichloromethane, chloroform, carbon tetrachloride and 1,2-dichloroethane. Examples of useful silicon compounds include chlorotrimethylsilane, chlorotriethylsilane, chlorobutyldimethylsilane, chloroethyldimethylsilane, etc. Examples of preferable bases are amines such as triethylamine, N,N-diethylaniline, N-methylmorpholine, pyridine and 4-dimethylaminopyridine. The silicon compound and the base are preferably used in an equimolar to excess proportion relative to the compound (16), respectively. The reaction is usually carried out at approximately room temperature to the reflux temperature for about 0.5–10 hours.

[Reaction scheme-6]

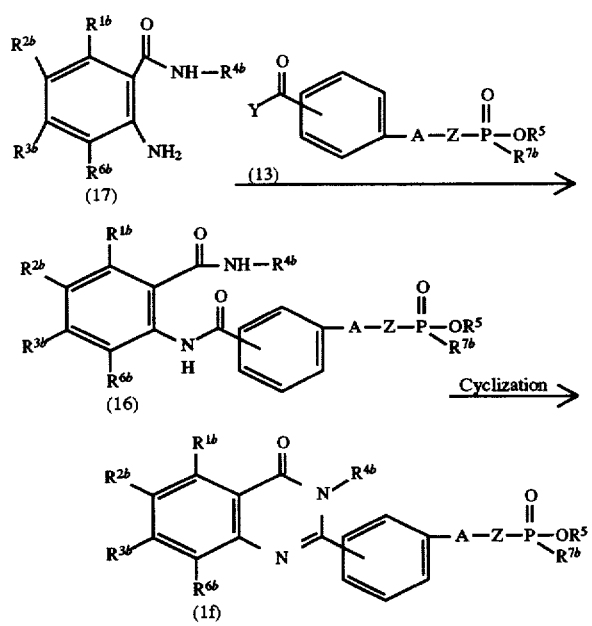

wherein $R^{1b}$, $R^{2b}$, $R^{3b}$, $R^{4b}$, $R^5$, $R^{6b}$, $R^{7b}$, A, Y and Z are as defined hereinabove.

In Reaction scheme-6, the reaction between the compound (17) and acid halide (13) can be carried out in the presence of an acid acceptor (base) in an inert solvent. Examples of useful inert solvents are aromatic or aliphatic hydrocarbons such as benzene, toluene, xylene and petroleum ether, ethers such as diethyl ether, ketones such as acetone, methyl ethyl ketone and acetophenone, and halogenated hydrocarbons such as dichloromethane, chloroform, carbon tetrachloride and 1,2-dichloroethane. Examples of useful acid acceptors (bases) are amines such as triethylamine, N,N-diethylaniline, N-methylmorpholine, pyridine and 4-dimethylaminopyridine. The acid halide (13) is preferably used in an equimolar to small excess proportion relative to the compound (17). The acid acceptor (base) is preferably used in an equimolar to excess proportion relative to the compound (17). The reaction usually goes to completion at about 0° C. to room temperature in about 0.5–10 hours.

The compound (16) thus obtained can be converted into the compound (1f) of the invention using the cyclization reaction shown in Reaction scheme-5.

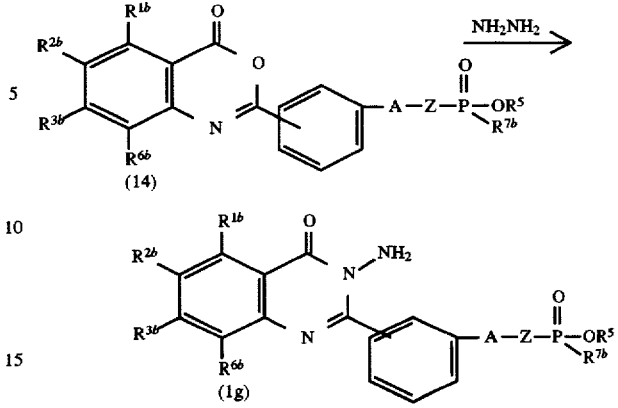

wherein $R^{1b}$, $R^{2b}$, $R^{3b}$, $R^5$, $R^{7b}$, A and Z are as defined hereinabove.

As shown in Reaction scheme-7, the compound (1g) of the invention can be obtained by treating the compound (14) with hydrazine. The reaction can be carried out in the presence of an base such as triethylamine, N,N-dimethylaniline, N-methylmorpholine, pyridine or 4-dimethylaminopyridine without using any solvent or in an inert solvent such as THF, methanol or 1,4-dioxane. The amount of hydrazine to be used is preferably 1 to 2 moles per mole of the compound (14). The base is preferably used in an equimolar to an excess proportion relative to the compound (14). The reaction is usually carried out at about room temperature to the reflux temperature for about 2–20 hours. The compound (14) is the same as the intermediate shown in Reaction scheme-5.

[Reaction scheme-8]

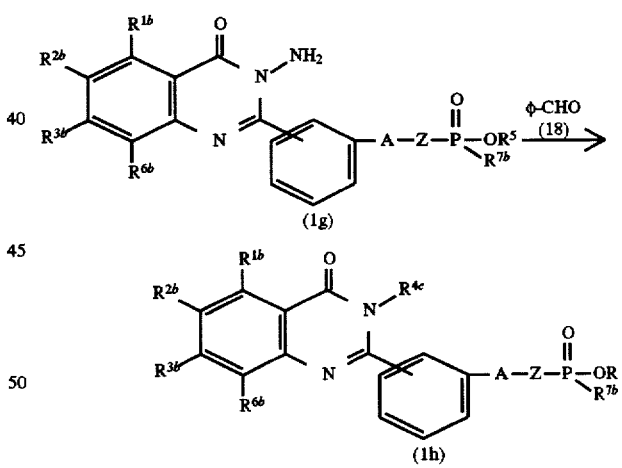

wherein $R^{1b}$, $R^{2b}$, $R^{3b}$, $R^5$, $R^{6b}$, $R^{7b}$, A and Z are as defined hereinabove, φ represents a phenyl group optionally having lower alkoxy or a pyridyl group, $R^{4c}$ represents a benzylideneamino group optionally having lower alkoxy on the phenyl ring or a pyridylmethylideneamino group.

As shown in Reaction scheme-8, the compound (1h) of the invention can be obtained by reacting the compound (1g) of the invention with an aldehyde (18). The reaction can be carried out using about 1 to 1.2 moles of the aldehyde (18) per mole of the compound (1g) in the presence of a small amount of an acid catalyst such as concentrated hydrochloric acid, concentrated sulfonic acid or p-toluenesulfonic acid without using any solvent or in an inert solvent such as THF, methanol or 1,4-dioxane. It is preferable that the reaction temperature be approximately room temperature to the reflux temperature and the reaction time be about 2–30 hours.

[Reaction scheme-9]

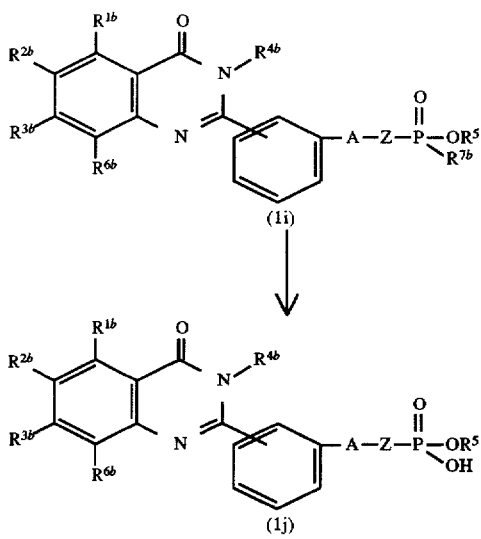

(1i)

↓

(1j)

wherein $R^{1b}$, $R^{2b}$, $R^{3b}$, $R^{4b}$, $R^5$, $R^{6b}$, $R^{7a}$, A and Z are as defined hereinabove.

According to the method shown in Reaction scheme-9, the compound (1i) is reacted with a lithium halide such as lithium bromide, lithium chloride or lithium iodide and post-treated with an aqueous solution of mineral acid such as hydrochloric acid or sulfonic acid to give the objective compound (1j) as partially hydrolyzed. The reaction can be carried out using at least 5 moles of lithium halide per mole of the compound (1i) in an inert solvent such as acetonitrile or DMF at room temperature to the reflux temperature for about 10–100 hours.

[Reaction scheme-10]

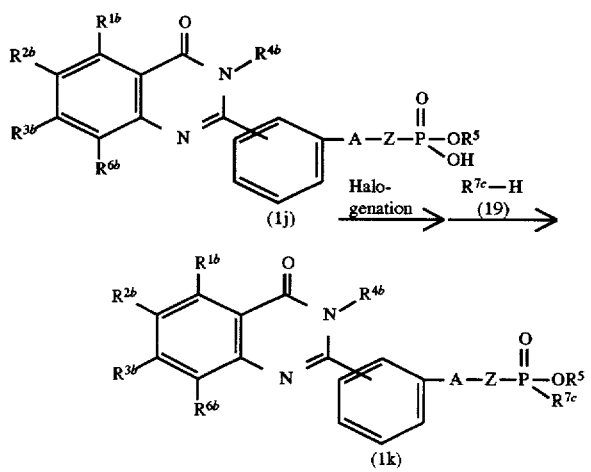

(1j)

Halogenation → $R^{7c}$—H (19) →

(1k)

wherein $R^{1b}$, $R^{2b}$, $R^{3b}$, $R^{4b}$, $R^5$, $R^{6b}$, A and Z are as defined hereinabove. $R^{7c}$ represents a phenyl(lower)alkylamino group or a phenyl(lower)alkoxy group optionally having halogen on the phenyl ring.

According to Reaction scheme-10, the compound (1j) is halogenated and then reacted with the compound. (19) to give the compound (1k).

The halogenation reaction can be carried out using about 1 to 1.2 moles of a halogenating agent such as thionyl chloride or phosphorus pentachloride per mole of the compound (1j) without using any solvent or in an inert solvent such as dichloromethane, chloroform or DMF at approximately room temperature to the reflux temperature for about 0.5–2 hours.

The compound (19) and a base such as pyridine, triethylamine or diazabicylo[5,4,0]undeca-7-ene (DBU) are then added to the reaction mixture obtained above in an amount of about 1–10 moles per mole of the starting compound respectively and the reaction goes to completion at 0° C. to room temperature in about 1 to 20 hours, giving the desired compound (1k).

[Reaction scheme-11]

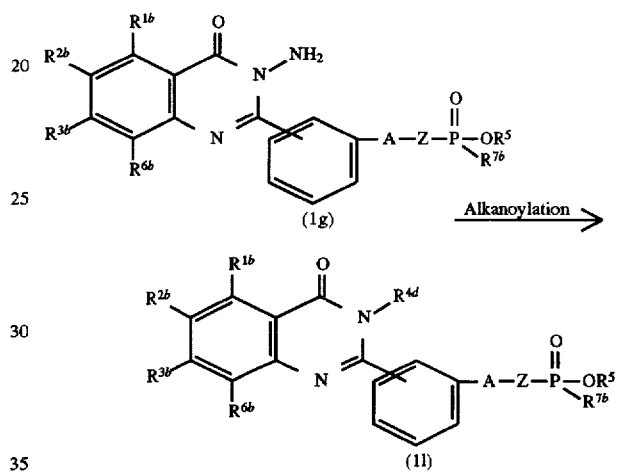

(1g)

Alkanoylation →

(1l)

wherein $R^{1b}$, $R^{2b}$, $R^{3b}$, $R^5$, $R^{6b}$, $R^{7b}$ A and Z are as defined hereinabove and $R^{4d}$ represents a di(lower)alkanoylamino group.

As shown in Reaction scheme-11, the compound (1l) can be obtained by alkanoylizing the compound (1g). The reaction can be carried out using an alkanoylizing agent without using any solvent or in an inert solvent such as pyridine, lutidine, DMF or DMA. Examples of useful alkanoylizing agents are acid anhydrides such as acetic anhydride, propionic anhydride, lactic anhydride, valeric anhydride, hexanoic anhydride and heptanoic anhydride or acid halides such as acetyl chloride, propionyl chloride, butyryl chloride, valeryl chloride, hexanoyl chloride and heptanoyl chloride. These alkanoylizing agents are preferably used in an amount of 1 to 10 equivalents relative to the compound (1g). The reaction goes to completion at approximately room temperature to 100° C. in about 3–30 hours.

[Reaction scheme-12]

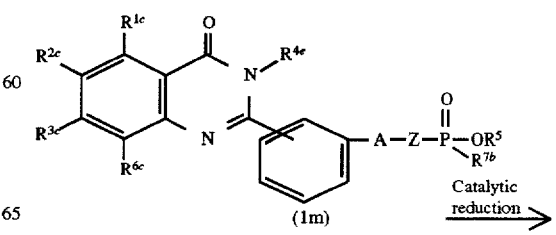

(1m)

Catalytic reduction →

-continued

|Reaction scheme-12|

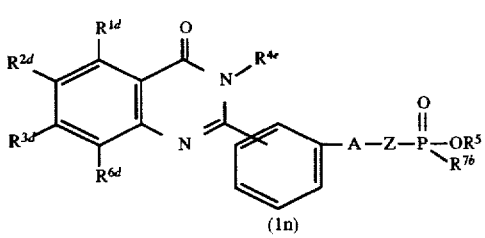

(1n)

wherein $R^5$, $R^{7b}$, A and Z are as defined hereinabove, at least one of the groups $R^{1c}$, $R^{2c}$, $R^{3c}$ and $R^{6c}$ represents a nitro group and the rest independently represent a hydrogen atom, a lower alkyl group, a halogen atom, a lower alkoxy group or a cyano group, $R^{4e}$ represents a phenyl group, a lower alkyl group, a phenyl(lower)alkyl group optionally substituted by halogen on the phenyl ring, a carboxy(lower)alkyl group, a (lower)alkoxycarboxyl(lower)alkyl group, a (lower)alkoxy(lower)alkyl group or a benzoyl(lower)alkyl group, and $R^{1d}$, $R^{2d}$, $R^{3d}$ and $R^{6d}$ represent the same groups as $R^{1c}$, $R^{2c}$, $R^{3c}$ and $R^{6c}$ with the exception that the group corresponding to $R^{1c}$, $R^{2c}$, $R^{3c}$ or $R^{6c}$ which represents a nitro group represents an amino group.

As shown in Reaction scheme-12, the compound (1n) can be obtained by subjecting the compound (1m) to catalytic reduction. The reaction can be carried out by stirring the compound (1m) and hydrogen gas in an inert solvent such as methanol, ethanol or ethyl acetate in the presence of a catalyst such as palladium-carbon or platinum oxide at room temperature for about 10 minutes to 2 hours.

|Reaction scheme-13|

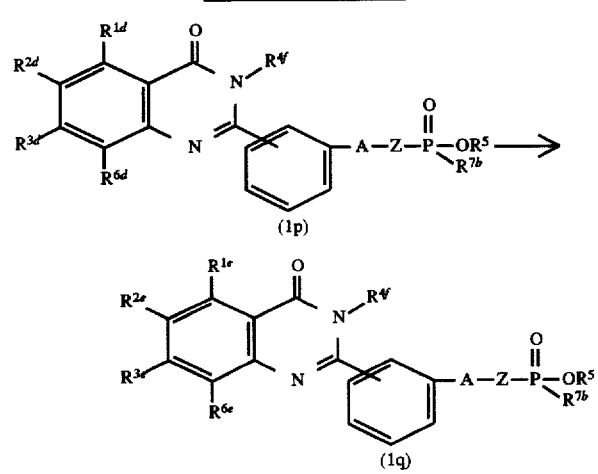

wherein $R^{1d}$, $R^{2d}$, $R^{3d}$, $R^5$, $R^{6d}$, $R^{7b}$ A and Z are as defined hereinabove, $R^{4f}$ represents a phenyl group, a lower alkyl group, a phenyl(lower)alkyl group optionally substituted by halogen on the phenyl ring, a (lower)alkoxycarbonyl(lower) alkyl group, a (lower)alkoxy(lower)alkyl group or a benzoyl (lower)alkyl group, $R^{1e}$, $R^{2e}$, $R^{3e}$ and $R^{6e}$ represent the same groups as $R^{1d}$, $R^{2d}$, $R^{3d}$ and $R^{6d}$ with the exception that the group corresponding to $R^{1d}$, $R^{2d}$, $R^{3d}$ or $R^{6d}$ which represents an amino group represents a benzoylamino group or a phenysulfonylamino group.

As shown in Reaction scheme-13, the compound (1p) can be converted into the compound (1q) by reacting the compound (1p) with a benzenesulfonyl halide such as benzenesulfonyl chloride or a benzoyl halide such as benzoyl chloride in an inert solvent such as pyridine, lutidine or triethylamine. The benzenesulfonyl halide or benzoyl halide is preferably used in an amount of about 1 to 3 moles per mole of the compound (1p). The reaction usually goes to completion at about 0° C. to room temperature in about 30 minutes to 24 hours.

The objective compounds in each of the above processes or compounds of the invention can be easily isolated and purified by conventional separation procedures. Such procedures include adsorption chromatography, preparative thin-layer chromatography, recrystallization, solvent extraction and so on.

The pharmaceutical composition containing the compound of the invention as an active ingredient can be made into general forms of medicine, using suitable pharmaceutically acceptable carriers. Useful pharmaceutically acceptable carriers include various conventional diluents or excipients such as fillers, volume builders, binders, humectants, disintegrators, surfactants, lubricants, etc. and are selectively employed according to the desired unit dosage form.

The above pharmaceutical composition can be provided in a variety of unit dosage forms according to the intended medical treatment. Typical examples are tablets, pills, powders, solutions, suspensions, emulsions, granules, capsules, suppositories, and injections (solutions, suspensions, etc.).

The molding of tablets can be made using, as said pharmaceutically acceptable carriers, an excipient such as lactose, sucrose, sodium chloride, glucose, urea, starch, calcium carbonate, kaolin, crystalline cellulose, silicic acid, potassium phosphate, etc., a binder such as water, ethanol, propanol, simple syrup, glucose syrup, a starch solution, a gelatin solution, carboxymethyl cellulose, hydroxypropyl cellulose, methyl cellulose, polyvinylpyrrolidone, etc., a disintegrator such as carboxymethyl cellulose sodium, carboxymethyl cellulose calcium, low-substituted hydroxypropyl cellulose, dry starch, sodium alginate, agar powder, laminaran powder, sodium hydrogen carbonate, calcium carbonate, etc., a surfactant such as polyoxyethylene sorbitan fatty acid ester, sodium lauryl sulfate, stearyl monoglyceride, etc., a disintegration inhibitor such as sucrose, stearin, cacao butter, hydrogenated oil, etc., an absorption promoter such as a quaternary ammonium base, sodium lauryl sulfate, etc., a humectant such as glycerin, starch, etc., an adsorbent such as starch, lactose, kaolin, bentonite, colloidal silica, etc., and a lubricant such as purified talc, salts of stearic acid, boric acid powder, polyethylene glycol, etc. Furthermore, such tablets can be coated, if necessary, to provide sugar-coated tablets, gelatin-coated tablets, enteric tablets, film-coated tablets, etc. or be processed into double-layer or multiple-layer tablets.

In the manufacture of pills, various excipients such as glucose, lactose, starch, cacao butter, hydrogenated vegetable oil, kaolin, talc, etc., binders such as gum arabic powder, tragacanth powder, gelatin, ethanol, etc. and disintegrators such as laminaran, starch, etc. can be employed as pharmaceutically acceptable carriers.

The suppositories can be manufactured using polyethylene glycol, cacao butter, higher alcohols or their esters, gelatin, semisynthetic glyceride, etc. as pharmaceutically acceptable carriers.

The capsules can be manufactured in conventional manners by blending the active ingredient compound of the invention with pharmaceutically acceptable carrier(s) as mentioned above and filling the resulting composition into hard gelatin capsule shells, soft capsule shells or the like.

When the compound of the invention is to be provided in an injectable form such as a solution, emulsion or suspension, the preparation is preferably sterilized and rendered isotonic with respect to the blood. As the diluent for use in such a preparation, water, ethyl alcohol, macrogols, propylene glycol, ethoxylated isostearyl alcohol, polyoxyisostearyl alcohol, polyoxyethylene sorbitan fatty acid esters, etc. can be mentioned. In this operation, a sufficient amount of sodium chloride, glucose, glycerin or the like may be added to the pharmaceutical composition to provide an isotonic solution. Conventional solubilizers, buffers, local anesthetics, etc. can also be added.

Further, coloring agents, preservatives, perfumes, flavors, sweeteners or other pharmaceutically active substances can be optionally incorporated in various dosage forms of the pharmaceutical composition.

There is no particular limitation on the administration method for said pharmaceutical compositions. Thus, a proper method can be selected according to the particular dosage form, patient's age, sex and other conditions, severity of disease, etc. For example, said tablets, pills, solutions, suspensions, emulsions, granules and capsules are administered by the oral route. The injections are administered singly or in admixture with glucose, amino acid or like conventional infusions by the intravenous route or, if necessary, administered singly by the intramuscular, intradermal, subcutaneous or intraperitoneal route. The suppositories are administered intrarectally.

The proportion of the active ingredient compound of the formula (1) of the invention in the pharmaceutical composition is not critical but can be liberally selected from a broad range. However, it is generally preferable that the compound accounts for about 1 to 70 weight % of the final composition. The dosing amount of the pharmaceutical composition can be selected according to the selected administration method, patient's age, sex and other conditions, severity of disease, etc. The dosage of the compound of the invention as the active ingredient is preferably about 0.05–100 mg per kg body weight a day, and this amount can be administered in 1 to 4 divided doses.

BEST MODE FOR PRACTICING THE INVENTION

To clarify the invention in more detail, Preparation Examples for the compounds of the invention are given below as Examples, followed by Pharmacological Test Examples and Formulation Examples using the compounds of the invention.

EXAMPLE 1

Preparation of diethyl 4-(3-phenyl-4(3H)-quinazolinon-2-yl)benzylphosphonate

A 0.62 g quantity of 2-(4-methylphenyl)-3-phenyl-4(3H)-quinazolinone, 0.39 g of N-bromosuccinimide (NBS) and 0.05 g of benzoyl peroxide were suspended in 20 ml of benzene and refluxed with heating for 10 hours. After adding 50 ml of water, the reaction mixture was extracted with chloroform. The chloroform layer was washed with water and dried over anhydrous sodium sulfate and the solvent was distilled off under reduced pressure to give 2-(4-bromomethylphenyl)-3-phenyl-4(3H)-quinazolinone as light yellow crude crystals.

The crude crystals were suspended in 3 ml of triethyl phosphite and stirred with heating at 150° C. for 1 hour. After distilling off an excess of triethyl phosphite under reduced pressure, the residue was purified by silica gel column chromatography (eluent: chloroform: ethyl acetate= 1:1). The crude crystals thus obtained were recrystallized from benzene-n-hexane to provide 0.45 g of the title compound as colorless crystals.

Table 1 shows the chemical structure and physical property (melting point) of the compound obtained.

EXAMPLE 2

Preparation of diethyl 4-(3-methyl-4(3H)-quinazolinon-2-yl)benzylphosphonate

Diethyl 4-|N-(2-cyanophenyl)carbamoyl| benzylphosphonate (11.2 g) was dissolved in 100 ml of THF and cooled with ice water. After adding 50 ml of a 30% hydrogen peroxide aqueous solution containing 1.2 g of sodium hydroxide dropwise, the reaction mixture was stirred at room temperature for 16 hours. Saturated brine (50 ml) was added, and the reaction mixture was extracted with chloroform. The chloroform layer was dried over magnesium sulfate and the solvent was distilled off under reduced pressure. The residue was dissolved in 150 ml of ethanol and 20 ml of a 2N sodium hydroxide solution and stirred at room temperature for 6 hours. Saturated brine (150 ml) was added, and the reaction mixture was extracted with chloroform. The chloroform layer was dried over magnesium sulfate, and then the solvent was distilled off under reduced pressure. The residue was recrystallized with methylene chloride-diethyl ether to give 5.9 g of diethyl 4-(4-hydroxyquinazolin-2-yl)benzylphosphonate as colorless crystals.

A 5.9 g quantity of diethyl 4-(4-hydroxyquinazolin-2-yl) benzylphosphonate, 1.8 g of potassium tert-butoxide and 2.3 g of methyl iodide were suspended in 100 ml of anhydrous methanol and stirred with heating at 40° C. for 16 hours. After completion of the reaction, the solvent was distilled off under reduced pressure. The residue was purified by silica gel column chromatography (eluent: methylene chloride: methanol=100:1) and the crude crystals thus obtained were recrystallized from methylene chloride-n-hexane to provide 3.0 g of the title compound as colorless crystals.

Table 1 shows the chemical structure and physical property (melting point) of the compound obtained.

EXAMPLES 3–23

The compounds shown in Table 1 were synthesized in the same manner as in Example 2. The chemical structures and physical properties of the compounds obtained are also shown in Table 1.

EXAMPLES 24 and 25

Preparation of diethyl 4-(5-fluoro-3-methyl-4(3H)-quinazolinon-2-yl)benzylthiophosphonate and diethyl 4-(5-fluoro-3-methyl-4(3H)-quinazolinethion-2-yl) benzylthiophosphonate The compound obtained in Example 3 (3.9 g) and a Lawesson's Reagent (4.5 g) were suspended in 50 ml of toluene and refluxed with heating for 2 hours. After completion of the reaction, the solvent was distilled off under reduced pressure. The residue was purified by silica gel column chromatography (eluent: methylene chloride) and recrystallized from diethyl ether-n-hexane.

From the latter fraction, 0.5 g of diethyl 4-(5-fluoro-3-methyl-4(3H)-quinazolinon-2-yl)benzylthiophosphonate was obtained as light yellow crystals (Example 24).

From the former fraction, 0.8 g of diethyl 4-(5-fluoro-3-methyl-4(3H)-quinazolinethion-2-yl) benzylthiophosphonate was obtained (Example 25).

Table 1 shows the chemical structures and physical properties of the compounds obtained.

EXAMPLE 26

Preparation of diethyl 4-(7-chloro-3-methyl-4(3H)-quinazolinon-2-yl)benzylphosphonate 2-Amino-4-chlorobenzoic acid (5.2 g) was suspended in 60 ml of concentrated hydrochloric acid and 60 ml of distilled water, and ice-cooled. After adding 30 ml of a 1.1M sodium nitrite aqueous solution, 60 ml of a saturated sodium acetate aqueous solution containing 2.0 g of sodium azide was also added to the reaction mixture. The resulting brown precipitate was collected by filtration to give 3.6 g of 2-azide-4-chlorobenzoic acid.

2-Azide-4-chlorobenzoic acid (2.0 g) was suspended in 11.9 g of thionyl chloride and refluxed with heating at 80° C. for 1 hour. After completion of the reaction, unreacted thionyl chloride was distilled off under reduced pressure and the residue was dissolved in 50 ml of benzene. Diethyl 4-(N-methylcarbamoyl)benzylphosphonate (2.9 g) and triethylamine (1.0 g) were added, and the reaction mixture was refluxed with heating at 80° C. for 15 hours. After completion of the reaction, the precipitate was separated by filtration and the solvent was distilled off under reduced pressure. The residue was purified by silica gel column chromatography (eluent: chloroform) and recrystallized from chloroform-n-hexane to provide 1.2 g of an imide as colorless crystals.

The imide (0.9 g) and triphenylphosphine (0.5 g) were dissolved in 10 ml of xylene and stirred in nitrogen atmosphere at room temperature for 1 hour. After completion of the reaction, the solvent was distilled off under reduced pressure and the residue was recrystallized from diethyl ether to give 0.8 g of the objective compound as colorless crystals. Table 1 shows the chemical structure and physical property (melting point) of the compound obtained.

EXAMPLES 27–42

The compounds shown in Table 2 were synthesized in the same manner as in Example 2. Table 2 also shows the chemical structures and physical properties (melting points) of the compounds obtained.

EXAMPLES 43 and 44

The compounds shown in Table 2 were synthesized in the same manner as in Example 1. Table 2 also shows the chemical structures and physical properties (melting points) of the compounds obtained.

TABLE 1

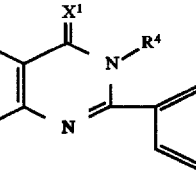

Et: Ethyl group, iPr: Isopropyl group, Ph: Phenyl group

| Example | $R^1$ | $R^2$ | $R^3$ | $R^4$ | $OR^5 = R^7$ | $X^1$ | $X^2$ | Melting point (°C.) |
|---|---|---|---|---|---|---|---|---|
| 1 | H | H | H | Ph | OEt | O | O | 156.0–156.5 |
| 2 | H | H | H | $CH_3$ | OEt | O | O | 128–129 |
| 3 | F | H | H | $CH_3$ | OEt | O | O | 155–156 |
| 4 | F | H | H | $CH_2Ph$ | OEt | O | O | 96–97 |
| 5 | Cl | H | H | $CH_3$ | OEt | O | O | 135–136 |
| 6 | H | Br | H | $CH_3$ | OEt | O | O | 99 (Dec.) |
| 7 | H | Br | H | Et | OEt | O | O | 77–78 |
| 8 | H | Br | H | $CH_2CH=CH_2$ | OEt | O | O | 65–66 |
| 9 | H | Br | H | $CH_2Ph$ | OEt | O | O | 120–121 |
| 10 | H | Br | H | 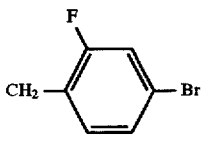 | OEt | O | O | 106–107 |
| 11 | H | Br | H | $CH_2CO_2H$ | OEt | O | O | 170 (Dec.) |
| 12 | H | Br | H | $CH_2CO_2Et$ | OEt | O | O | 149–150 |
| 13 | H | Br | H | $CH_3$ | O-iPr | O | O | 123–124 |
| 14 | H | $NO_2$ | H | $CH_3$ | OEt | O | O | 126–127 |
| 15 | H | $OCH_3$ | $OCH_3$ | $CH_3$ | $OCH_3$ | O | O | 193–194 |
| 16 | H | $OCH_3$ | $OCH_3$ | $CH_3$ | OEt | O | O | 147–148 |
| 17 | H | $OCH_3$ | $OCH_3$ | $CH_2Ph$ | OEt | O | O | 149–150 |
| 18 | H | $OCH_3$ | $OCH_3$ | 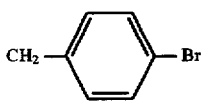 | OEt | O | O | 135–136 |
| 19 | H | $OCH_3$ | $OCH_3$ | (CH$_2$–C$_6$H$_4$–Br) | OEt | O | O | 103–104 |
| 20 | H | $OCH_3$ | $OCH_3$ | $CH_2CO_2H$ | OEt | O | O | 220 (Dec.) |

TABLE 1-continued

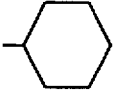

Et: Ethyl group, iPr: Isopropyl group, Ph: Phenyl group

| Example | R¹ | R² | R³ | R⁴ | OR⁵=R⁷ | X¹ | X² | Melting point (°C.) |
|---|---|---|---|---|---|---|---|---|
| 21 | H | OCH₃ | OCH₃ | CH₃ | O-iPr | O | O | 166–167 |
| 22 | H | OCH₃ | OCH₃ | CH₂Ph | O-iPr | O | O | 103–104 |
| 23 | H | OCH₃ | OCH₃ | CH₂CH₂Ph | O-iPr | O | O | 165–166 |
| 24 | F | H | H | CH₃ | OEt | O | S | 142–143 |
| 25 | F | H | H | CH₃ | OEt | S | S | 139–140 |
| 26 | H | H | Cl | CH₃ | OEt | O | O | 142–142.5 |

TABLE 2

Et: Ethyl group, Ph: Phenyl group

| Example | R¹ | R² | R³ | R⁴ | OR⁵=R⁷ | R⁶ | X¹ | X² | Melting point (°C.) |
|---|---|---|---|---|---|---|---|---|---|
| 27 | H | H | NO₂ | CH₃ | OEt | H | O | O | 125.5–126.5 |
| 28 | H | H | Br | CH₃ | OEt | H | O | O | 149.5–150.5 |
| 29 | H | H | OCH₃ | CH₃ | OEt | Br | O | O | 155–156 |
| 30 | H | H | CF₃ | CH₃ | OEt | H | O | O | 51–52 |
| 31 | H | H | F | CH₃ | OEt | H | O | O | 83–84 |
| 32 | H | H | H | CH₃ | OEt | OCH₃ | O | O | 99–100.5 |
| 33 | H | H | Cl | CH₂Ph | OEt | H | O | O | 88–89 |
| 34 | H | H | Cl | CH₂COOH | OEt | H | O | O | 232 (Dec.) |
| 35 | H | OCH₃ | OCH₃ | CH₃ | OEt | OCH₃ | O | O | 97–98 |
| 36 | H | I | H | CH₃ | OEt | H | O | O | 143–144 |
| 37 | H | H | Cl | C₂H₅ | OEt | H | O | O | 115–117 |
| 38 | H | H | Cl | cyclohexyl | OEt | H | O | O | 85–87 |
| 39 | H | H | Cl | CH₂OCH₃ | OEt | H | O | O | 123–124 |
| 40 | H | H | Cl | CH₂C≡CH | OEt | H | O | O | 143–146 |
| 41 | H | H | Cl | CH₂CH₂Ph | OEt | H | O | O | 113–115 |
| 42 | H | H | Cl | CH₂COPh | OEt | H | O | O | 130–134 |
| 43 | Br | H | H | CH₃ | OEt | H | O | O | 79–80 |
| 44 | H | H | Br | CH₃ | OMe | H | O | O | 116–117 |

EXAMPLE 45

Preparation of diethyl 4-(7-chloro-3-methyl-4(3H)-quinazolinon-2-yl)benzylphosphonate (Step 1)

4-[(Diethoxyphosphoryl)methyl]benzoic acid (600 g) was suspended in 250 ml of dichloromethane and 250 ml of DMF. After adding 260 g of thionyl chloride dropwise, the mixture was stirred at 40° C. for 2 hours.

The reaction mixture was slowly added dropwise to 1200 ml of pyridine containing 188 g of 4-chloroanthranilic acid with ice-cooling and stirring.

The reaction mixture was stirred at room temperature for 20 hours and then 1500 ml of distilled water was added. The crystals precipitated were collected by filtration to give 233 g of diethyl 4-(7-chloro-4H-1,3-benzoxazin-4-on-2-yl) benzylphosphonate.

The filtrate was washed with 3N hydrochloric acid and distilled water in this order and dried over magnesium sulfate. The solvent was distilled off under reduced pressure and the residue was recrystallized from dichloromethane-diethyl ether to provide 102 g of diethyl 4-(7-chloro-4H-1, 3-benzoxazin-4-on-2-yl)benzyl-phosphonate.

(Step 2)

The compound obtained in step 1 (102 g) was dissolved in 750 ml of THF. After adding 58 ml of a 40% methylamine aqueous solution, the mixture was stirred at room temperature for 1 hour. Distilled water was added to the residue, and the crystals precipitated were collected by filtration to give 98 g of diethyl 4-{[7-chloro-2-(N-methylcarbamoyl)phenyl] carbamoyl}benzylphosphonate.

(Step 3)

The compound obtained in step 2 (80 g) was dissolved in 221 g of triethylamine and 2000 ml of dichloromethane. While the solution was stirred at room temperature, 87 g of chlorotrimethylsilane was slowly added dropwise. After completion of the dropping, the mixture was stirred with heating at 40° C. for 17 hours. After completion of the reaction, the reaction mixture was condensed, 1000 ml of 1N hydrochloric acid was added to the residue, and the mixture was extracted with dichloromethane. The organic layer was dried over magnesium sulfate and the solvent was distilled off under reduced pressure. Diisopropyl ether was added to the residue and the resulting crystals were collected by filtration. The crude crystals were recrystallized from ethanol-water to give 88.6 g of the desired diethyl 4-(7-chloro-3-methyl-4(3H)-quinazolinon-2-yl)benzylphosphonate.

It was confirmed from the melting point and $^1$H-NMR-spectrum data that the compound thus obtained is the same compound as produced in Example 26.

EXAMPLES 46–51

The compounds shown in Table 3 were synthesized in the same manner as in Example 45. Table 3 also shows the chemical structures and physical properties (melting points) of the compounds obtained.

EXAMPLE 52

Preparation of diethyl 4-(7-chloro-3-methyl-4(3H)-quinazolinon-2-yl)benzylphosphonate (Step 1)

4-[(Diethoxyphosphoryl)methyl]benzoic acid (27.2 g) was suspended in 60 ml of dichloromethane and 2 ml of DMF. After adding 13.1 g of thionyl chloride, the mixture was refluxed for 1 hour. After completion of the reaction, the reaction mixture was let cool and slowly added dropwise to a solution of 18.5 g of 2-(N-methylcarbamoyl)-5-chloroaniline in 50 ml of pyridine and 30 ml of dichloromethane with ice-cooling and stirring. After completion of the dropping, the mixture was stirred at room temperature for 48 hours, followed by addition of 50 ml of water. The crystals thus precipitated were collected by filtration, washed with water well and dried to give 23.6 g of diethyl 4-[[7-chloro-2-(N-methylcarbamoyl)phenyl]carbamoyl] benzylphosphonate.

(Step 2)

The compound obtained in the above Step 1 was reacted in the same manner as shown in Step 3 of Example 45 to give the objective compound as crystals.

It was confirmed from the melting point and 1H-NMR-spectrum data that the compound thus obtained is the same compound as produced in Examples 26 and 45.

EXAMPLES 53–56

The compounds shown in Table 3 were synthesized in the same manner as in Example 52. Table 3 also shows the chemical structures and physical properties (melting points) of the compounds obtained. As to oil compounds, $^1$H-NMR spectrum data (δ: ppm) are shown.

EXAMPLE 57

Preparation of diethyl 4-(3-amino-7-chloro-4(3H)-quinazolinon-2-yl)benzylphosphonate The compound obtained in Example 45, Step 1 (20.0 g) and hydrazine hydrate (2.5 g) were suspended in 200 ml of pyridine and refluxed for 16 hours. After completion of the reaction, the reaction mixture was condensed under reduced pressure. The residue was diluted with dichloromethane and washed with 2N hydrochloric acid, distilled water and saturated brine in this order. The organic layer was dried over anhydrous magnesium sulfate and condensed under reduced pressure. The residue was purified by silica gel column chromatography (eluent: dichloromethane:methanol=50:1) and the crystals obtained were recrystallized from dichloromethane-diethyl ether to give 14.1 g of the desired compound as colorless crystals.

Table 3 shows the chemical structure and physical property (melting point) of the compound obtained.

EXAMPLE 58

Preparation of diethyl 4-(3-N-benzylideneamino-7-chloro-4 (3H)-quinazolinon-2-yl)benzylphosphonate The compound obtained in Example 56 (2.0 g), 1.0 g of benzaldehyde and a catalytic amount of concentrated hydrochloric acid were suspended in 50 ml of methanol and stirred at room temperature for 24 hours. After completion of the reaction, the reaction mixture was concentrated under reduced pressure and crude crystals thus obtained were recrystallized from dichloromethane-diethyl ether to give 1.6 g of the desired compound as colorless crystals. Table 3 shows the chemical structure and physical property (melting point) of the compound obtained.

EXAMPLES 59 and 60

The compounds shown in Table 3 were synthesized in the same manner as in Example 58. Table 3 also shows the chemical structures and physical properties (melting points) of the compounds obtained.

EXAMPLE 61

Preparation of ethyl 4-(7-chloro-3-methyl-4(3H)-quinazolinon-2-yl)benzylphosphonate The compound obtained in Example 26 (70 g) was dissolved in 800 ml of acetonitrile. After adding 118 g of lithium chloride, the reaction mixture was refluxed for 3 days. After completion of the reaction, the precipitate was collected by filtration and dissolved in 2.5 l of distilled water. The solution was made acid by adding 2N hydrochloric acid. The crystals precipitated were collected by filtration and dried to give 58 g of the desired compound as crystals. Table 3 also shows the chemical structure and physical property (melting point) of the compound obtained.

EXAMPLE 62

Preparation of ethyl P-[4-(7-chloro-3-methyl-4(3H)-quinazolinon-2-yl)benzyl]-N-benzylphosphonamidate The compound obtained in Example 61 (0.50 g), 1 ml of DMF and 0.15 g of thionyl chloride were suspended in 10 ml of dichloromethane and refluxed for 3 hours. After completion of the reaction, the reaction mixture was allowed to cool, 10 ml of dichloromethane containing 0.14 g of benzylamine and 0.58 g of DBU was added dropwise, and the mixture was stirred at room temperature for 18 hours. After the reaction, the organic layer was washed with diluted hydrochloric acid, distilled water and saturated brine in this order, dried over anhydrous magnesium sulfate, and concentrated under reduced pressure. The residue thus obtained was purified by silica gel column chromatography (eluent: dichloromethane: methanol=30:1) and recrystallized from ethyl acetate-n-hexane to provide 0.28 g of the desired compound as colorless crystals. Table 3 shows the chemical structure and physical property (melting point) of the compound obtained.

EXAMPLES 63 and 64

The compounds shown in Table 3 were synthesized in the same manner as in Example 62. Table 3 also shows the chemical structures and physical properties (melting points) of the compounds obtained. As to the oil compound, 1H-NMR spectrum data (δ: ppm) are shown.

EXAMPLE 65
Preparation of diethyl 4-(7-chloro-3-N,N-diacetylamino-4(3H)-quinazolinon-2-yl)benzylphosphonate The compound obtained in Example 57 (3.0 g) and anhydrous acetic acid (2.2 g) were suspended in 20 ml of pyridine and refluxed at room temperature for 18 hours. After completion of the reaction, the reaction mixture was concentrated under reduced pressure and the residue was diluted with dichloromethane and washed with distilled water. The organic layer was dried over anhydrous magnesium sulfate and condensed under reduced pressure. The residue was purified by silica gel column chromatography (eluent: dichloromethane: methanol=50:1) and recrystallized from dichloromethane-n-hexane to provide 2.3 g of the desired compound as colorless crystals. Table 3 shows the chemical structure and property (melting point) of the compound obtained.

EXAMPLE 66
Preparation of diethyl 4-(7-amino-3-methyl-4(3H)-quinazolinon-2-yl)benzylphosphonate The compound obtained in Example 27 (15.8 g) was dissolved in 450 ml of refined ethanol. After adding 1.5 g of 5% paradium-carbon, the reaction mixture was stirred in hydrogen gas at room temperature for 30 minutes. After completion of the reaction, the paradium-carbon was filtered off and the filtrate was condensed under reduced pressure. The residue was purified by silica gel column chromatography (eluent: chloroform: methanol=20:1) and recrystallized from chloroform-diethyl ether to provide 9.8 g of the desired compound as colorless crystals. Table 3 shows the chemical structure and physical property (melting point) of the compound obtained.

EXAMPLE 67
Preparation of diethyl 4-(3-methyl-7-phenylsulfonylamino-4(3H)-quinazolinon-2-yl)benzylphosphonate Benzenesulfonyl chloride (0.57 ml) was slowly added dropwise at 0° C. to 10 ml of pyridine containing 1.5 g of the compound obtained in Example 66. The mixture was stirred at room temperature for 12 hours. After adding a saturated sodium bicarbonate solution, the reaction mixture was extracted with dichloromethane. The organic layer was washed with diluted hydrochloric acid, dried over anhydrous magnesium sulfate and concentrated under reduced pressure. The residue was recrystallized from diethyl ether to give 1.75 g of the desired compound as colorless crystals. Table 3 shows the chemical structure and physical property (melting point) of the compound obtained.

EXAMPLE 68

The compound shown in Table 3 was prepared in the same manner as in Example 67. Table 3 also shows the chemical structure and physical property (melting point) of the compound obtained.

TABLE 3

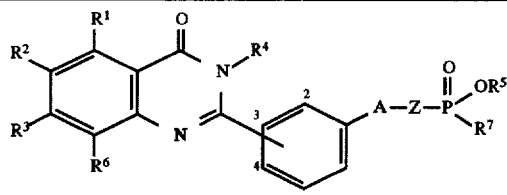

Me: Methyl group, Et: Ethyl group, iPr: Isopropyl group,
Ac: Acetyl group, Ph: Phenyl group

| Example | $R^1$ | $R^2$ | $R^3$ | $R^4$ | $R^5$ | $R^6$ | $R^7$ | A | Z | PB | Mp (°C.) |
|---|---|---|---|---|---|---|---|---|---|---|---|
| 46 | H | Br | Cl | Me | Et | H | OEt | SB* | $CH_2$ | 4 | 144–145 |
| 47 | H | Br | $NO_2$ | Me | Et | H | OEt | SB* | $CH_2$ | 4 | 177–178 |
| 48 | H | H | CN | Me | Et | H | OEt | SB* | $CH_2$ | 4 | 121–122 |
| 49 | H | H | Cl | Me | Me | H | OMe | SB* | $CH_2$ | 4 | 109–110 |
| 50 | H | H | Cl | Me | iPr | H | OiPr | SB* | $CH_2$ | 4 | 116–119 |
| 51 | H | Me | H | Me | Et | H | OEt | SB* | $CH_2$ | 4 | 117–118 |
| 53 | H | H | Cl | Me | Et | H | Ph | SB* | $CH_2$ | 4 | 192–193 |
| 54 | H | H | Cl | Me | Et | H | OEt | SB* | $CH_2$ | 3 | 66.5–67.5 |
| 55 | H | H | Cl | Me | Et | H | OEt | SB* | $CH_2$ | 2 | Oil NMR (1) |
| 56 | H | H | Cl | Me | Et | H | OEt | O | $C_2H_4$ | 4 | Oil NMR (2) |
| 57 | H | H | Cl | $NH_2$ | Et | H | OEt | SB* | $CH_2$ | 4 | 141–142 |
| 58 | H | H | Cl | N=CH—Ph | Et | H | OEt | SB* | $CH_2$ | 4 | 163–165 |
| 59 | H | H | Cl | N=CH—⟨C6H4⟩—OMe | Et | H | OEt | SB* | $CH_2$ | 4 | 132–133 |
| 60 | H | H | Cl | N=CH—(pyridyl) | Et | H | OEt | SB* | $CH_2$ | 4 | 120–121 |
| 61 | H | H | Cl | Me | Et | H | OH | SB* | $CH_2$ | 4 | 181–182 |

TABLE 3-continued

| | | | | | | | | | | | |
|---|---|---|---|---|---|---|---|---|---|---|---|
| 62 | H | H | Cl | Me | | Et | H | NH—CH$_2$—Ph | SB* | CH$_2$ | 4 | 150–151 |
| 63 | H | H | Cl | Me | | Et | H | 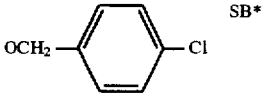 | SB* | CH$_2$ | 4 | 143–144 |
| 64 | H | H | Cl | Me | | Et | H | O—CH$_2$—Ph | SB* | CH$_2$ | 4 | Oil NMR (3) |
| 65 | H | H | Cl | N(Ac)$_2$ | | Et | H | OEt | SB* | CH$_2$ | 4 | 113–116 |
| 66 | H | H | NH$_2$ | Me | | Et | H | OEt | SB* | CH$_2$ | 4 | 177–178 (Dec.) |
| 67 | H | H | NHSO$_2$Ph | Me | | Et | H | OEt | SB* | CH$_2$ | 4 | 122–123 (Dec.) |
| 68 | H | H | NHCOPh | Me | | Et | H | OEt | SB* | CH$_2$ | 4 | 179.5–180.5 (Dec.) |

| Example | $^1$H-NMR($\delta$: ppm) [CDCl$_3$] |
|---|---|
| 55 | 1.18(6H, dt, J=4.7)<br>3.08(1H, dd, J=22.15)<br>3.44(3H, s), 3.67(1H, dd, J=22.15)<br>3.90–4.02(4H, m), 7.32–7.59(5H, m)<br>7.69(1H, d, J=2), 8.28(1H, d, J=9) |
| 56 | 1.37(6H, t, J=7), 2.35(2H, dt, J=19.7)<br>3.52(3H, s), 4.11–4.20(4H, m)<br>4.27–4.37(2H, m), 7.04(2H, d, J=9)<br>7.43(1H, dd, J=8.2), 7.53(2H, d, J=9)<br>7.71(1H, d, J=2), 8.24(1H, d, J=8) |
| 64 | 1.25(3H, t, J=7), 3.23(2H, d, J=22)<br>3.47(3H, s), 3.94–4.15(2H, m)<br>5.04(2H, d, J=9), 7.35–7.52(10H, m)<br>7.71(1H, d, J=2), 8.23(1H, d, J=9) |

SB* means "single bond"
PB means "position of bond".

Pharmacological Test Example 1

Using rats with Triton-induced hyperlipidemia, preventive and therapeutic effects of the compounds of the invention on hyperlipidemia were tested according to the method of Kuroda et al. [Biochem. Biophys. Acta., 489, 119 (1977)] as follows.

Five 6- to 7-week-old male Wistar rats (a test group) were intravenously injected in the tail with a solution of 300 mg per kg body weight of Triton (Triton WR 1339) in physiological saline and simultaneously dosed orally with 100 mg per kg body weight of a test compound as suspended in a 0.5% CMC-Na aqueous solution.

As a control group, five rats were injected with the above-mentioned Triton and orally dosed with a 0.5% CMC-Na solution free of the test compound.

Twenty four hours after the administration of Triton, blood samples were taken from the rats and the amount of triglyceride (TG) in the plasma was determined with the aid of Triglyceride G-Test Wako (product of Wako Pure Chemical Industries, Ltd.).

The TG decrease (%) in the plasma was calculated from TG amounts of the test group and the control group by the following equation. No food was given to the rats during the period from the Triton administration to the completion of the blood sampling, although they were free to drink water.

$$\text{TG decrease (\%) in the plasma} = \left[ 1 - \frac{\text{(Test group value)}}{\text{(Control group value)}} \right] \times 100$$

Table 4 shows the results.

TABLE 4

| Test compound (Example No.) | TG decrease in the plasma (%) |
|---|---|
| 6 | 35 |
| 7 | 42 |
| 8 | 43 |
| 9 | 54 |
| 14 | 29 |
| 15 | 41 |
| 16 | 86 |
| 17 | 85 |
| 21 | 81 |

It is apparent from Table 4 that all the test compounds according to the invention can reduce the amount of TG and are effective in preventing or treating hyperlipidemia.

Pharmacological Test Example 2

Hypoglycemic effects of the compounds of the invention were tested using mice as follows.

Five 8- to 10-week male KKAy mice (a test group) were free to take water and powder feed (CFR-1, product of Oriental Yeast Co., Ltd.) containing 0.1 wt. % of a test compound for four days. On day 5, blood samples were taken from their eyegrounds and the amount of blood glucose was determined using a glucose sensor (product of Daikin Industries, Co., Ltd.).

As a control group, five mice were provided with test compound-free feed. Blood glucose decrease (%) was calculated from glucose amounts of the control group and the test group by the following equation.

$$\text{Blood glucose decrease (\%)} = \left[1 - \frac{\text{(Test group value)}}{\text{(Control group value)}}\right] \times 100$$

Table 5 shows the results.

TABLE 5

| Test compound (Example No.) | Blood glucose decrease (%) |
|---|---|
| 3 | 23 |
| 26 | 30 |

It is apparent from Table 5 that the compounds of the invention have hypoglycemic effects and are effective in treating diabetes.

Pharmacological Test Example 3

Hypoglycemic effects of the compounds of the invention were tested using rats as follows.

Five 6-week-old male Wistar rats (a test group) were abdominally injected with 0.5 mg per kg body weight of dexamethasone (a Decadron S injection solution; product of Bannyu Pharmaceutical Co., Ltd.) once a day for four days. Also, immediately after each daily administration, 100 mg per kg body weight of a test compound as dissolved in a 5% gum arabic solution was orally administered. Four hours after the administration of dexamethasone on day 4, the rats were decapitated to take blood samples and the samples were subjected to centrifugation (3000 rpm, 4° C., 15 min.). The amount of glucose in the blood serum was determined with the aid of Glucose C II-Test Wako (product of Wako Pure Chemical Industries, Ltd.). The rats had free access to feed at first but were deprived of the food 24 hours before the blood sampling.

As a control group, five rats were orally dozed with a test compound-free 5% gum arabic solution, and as a normally-conditioned group, other five rats were given only free access to feed. The amounts of glucose in the blood serum of these groups were determined in the same manner as above. The blood glucose decrease (%) was determined from the glucose amounts of each of the three groups (the average values) by the following equation.

Blood glucose decrease (%) =

$$\frac{\text{(Control group value)} - \text{(Test group value)}}{\text{(Control group value)} - \text{(Normally-conditioned group value)}} \times 100$$

Table 6 shows the results.

TABLE 6

| Test compound (Example No.) | Blood glucose decrease (%) |
|---|---|
| 3 | 50 |
| 26 | 100 |
| 28 | 60 |
| 30 | 42 |
| 40 | 33 |
| 41 | 42 |
| 44 | 91 |
| 49 | 58 |
| 50 | 54 |
| 51 | 56 |
| 53 | 51 |

TABLE 6-continued

| Test compound (Example No.) | Blood glucose decrease (%) |
|---|---|
| 60 | 38 |
| 62 | 70 |

It is apparent from Table 6 that the compounds of the invention have excellent hypoglycemic effects and are effective in treating diabetes.

Formulation Example 1
Manufacture of tablets

Using the compound obtained in Example 26 as an active ingredient, tablets (2000 tablets) each containing 250 mg of the active ingredient were manufactured according to the following formula.

| Ingredient | Amount (g) |
|---|---|
| Compound of Example 26 | 500 |
| Lactose (product of Japanese pharmacopeia: JP) | 67 |
| Corn starch (JP) | 33 |
| Carboxymethyl cellulose calcium (JP) | 25 |
| Methylcellulose (JP) | 12 |
| Magnesium stearate (JP) | 3 |
| Total | 640 |

According to the above formula, the compound of Example 26, lactose, corn starch and carboxymethyl cellulose calcium were well blended and granulated using an aqueous solution of methyl cellulose. The granulated mixture was passed through a 24-mesh sieve and the granules under the sieve were mixed with magnesium stearate and compression-molded into the desired tablets.

Formulation Example 2
Manufacture of capsules

Using the compound obtained in Example 16 as an active ingredient, hard gelatin capsules (2000 units) each containing 250 mg of the active ingredient were manufactured according to the following formula.

| Ingredient | Amount (g) |
|---|---|
| Compound of Example 16 | 500 |
| Crystalline cellulose (JP) | 60 |
| Corn starch (JP) | 34 |
| Talc (JP) | 4 |
| Magnesium stearate (JP) | 2 |
| Total | 600 |

Thus, according to the above formula, the ingredients were reduced to fine powder and blended to give a homogeneous composition. This composition was filled into proper-sized gelatin capsule shells for oral administration to provide the desired capsules.

Typical examples of the compounds of the invention include the following compounds as well as those described above in examples.

Diisopropyl 4-(7-bromo-3-methyl-4(3H)-quinazolinon-2-yl)benzylphosphonate

Ethylmethyl 4-(7-chloro-3-methyl-4(3H)-quinazolinon-2-yl)benzylphosphonate

Ethylisopropyl 4-(7-chloro-3-methyl-4(3H)-quinazolinon-2-yl)benzylphosphonate

Isopropylmethyl 4-(7-chloro-3-methyl-4(3H)-quinazolinon-2-yl)benzylphosphonate

Methyl |4-(7-chloro-3-methyl-4(3H)-quinazolinon-2-yl)benzyl|-N-benzylamidophosphonate Isopropyl |4-(7-chloro-3-methyl-4(3H)-quinazolinon-2-yl)benzyl|-N-benzylamidophosphonate Methyl |4-(7-bromo-3-methyl-4(3H)-quinazolinon-2-yl)benzyl|-N-benzylamidophosphonate Ethyl |4-(7-bromo-3-methyl-4(3H)-quinazolinon-2-yl)benzyl|-N-benzylamidophosphonate Isopropyl |4-(7-bromo-3-methyl-4(3H)-quinazolinon-2-yl)benzyl|-N-benzylamidophosphonate Diethyl 4-(5-bromo-3-methyl-4(3H)-quinazolinon-2-yl)benzylphosphonate Diethyl 4-(5-iodo-3-methyl-4(3H)-quinazolinon-2-yl)benzylphosphonate Dimethyl 4-(5-fluoro-3-methyl-4(3H)-quinazolinon-2-yl)benzylphosphonate Diethyl 4-(5-fluoro-3-ethyl-4(3H)-quinazolinon-2-yl)benzylphosphonate Diisopropyl 4-(5-fluoro-3-methyl-4(3H)-quinazolinon-2-yl)benzylphosphonate

We claim:

1. A phosphonic ester derivative of the formula:

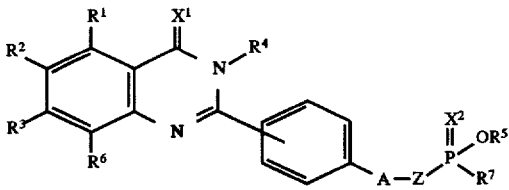

(1)

wherein $R^1$, $R^2$, $R^3$ and $R^6$ are the same or different and each represents a hydrogen atom, a lower alkyl group, a halogen atom, a nitro group, a lower alkoxy group, a cyano group, a phenylsulfonylamino group, a benzoylamino group, an amino group or a halogen-substituted lower alkyl group, $R^4$ represents a phenyl group, a lower alkyl group, a phenyl(lower)alkyl group optionally substituted by halogen on the phenyl ring, a lower alkenyl group, a carboxy(lower)alkyl group, a (lower)alkoxycarbonyl(lower)alkyl group, a (lower)alkoxy(lower)alkyl group, a lower alkynyl group, a benzoyl(lower)alkyl group, an amino group, a di(lower)alkanoylamino group, a benzylideneamino group optionally having lower alkoxy on the phenyl ring or a pyridylmethylideneamino group, $R^5$ represents a lower alkyl group, $R^7$ represents a lower alkoxy group, a hydroxyl group, a phenyl group, a phenyl(lower)alkoxy group optionally having halogen on the phenyl ring or a phenyl(lower)alkylamino group, $X^1$ and $X^2$ independently represent an oxygen atom or a sulfur atom, A represents an oxygen atom or a single bond, and Z represents a lower alkylene group.

2. A phosphonic ester derivative of the formula:

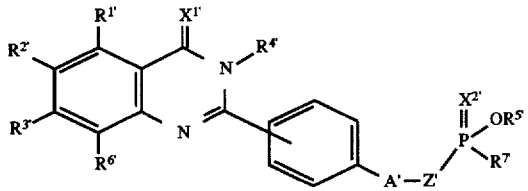

(1')

wherein $R^{1'}$ represents a hydrogen atom or a halogen atom, $R^{2'}$ represents a hydrogen atom, a lower alkyl group, a halogen atom, a nitro group or a lower alkoxy group, $R^{3'}$ represents a hydrogen atom, a halogen atom, a nitro group, a halogen-substituted lower alkyl group, a cyano group, a phenylsulfonylamino group, a benzoylamino group, an amino group or a lower alkoxy group, $R^{4'}$ represents a phenyl group, a lower alkyl group, a phenyl(lower)alkyl group optionally substituted by halogen on the phenyl ring, a lower alkenyl group, a carboxy(lower)alkyl group, a (lower)alkoxy-carbonyl(lower)alkyl group, a (lower)alkoxy (lower)alkyl group, a lower alkynyl group, a benzoyl(lower) alkyl group, an amino group, a di(lower)alkanoylamino group, a benzylideneamino group optionally having lower alkoxy on the phenyl ring or a pyridylmethylideneamino group, $R^{5'}$ represents a lower alkyl group, $R^{6'}$ represents a hydrogen atom, a lower alkoxy group or a halogen atom, $R^{7'}$ represents a lower alkoxy group, a hydroxyl group, a phenyl group, a phenyl(lower)alkoxy group optionally having halogen on the phenyl ring or a phenyl(lower)alkylamino group, $X^{1'}$ and $X^{2'}$ independently represent an oxygen atom or a sulfur atom, A' represents an oxygen atom or a single bond, Z' represents an ethylene group when A' represents an oxygen atom, and Z' represents a methylene group when A' represents a single bond.

3. A phosphonic ester derivative according to claim 1 represented by the formula:

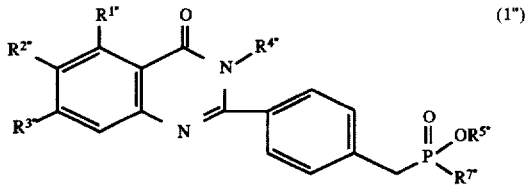

(1")

wherein $R^{1''}$ represents a hydrogen atom or a halogen atom, $R^{2''}$ represents a hydrogen atom, a halogen atom, a nitro group, a lower alkyl group or a lower alkoxy group, $R^{3''}$ represents a hydrogen atom, a halogen atom, a halogen-substituted lower alkyl group or a lower alkoxy group, $R^{4''}$ represents a lower alkyl group, a phenyl(lower)alkyl group, a lower alkynyl group, a pyridylmethylideneamino group or a lower alkenyl group, $R^{5''}$ represents a lower alkyl group, and $R^{7''}$ represents a lower alkoxy group, a phenyl group or a phenyl(lower)alkylamino group.

4. A phosphonic ester derivative according to claim 3 wherein $R^{1''}$ represents a hydrogen atom, $R^{2''}$ represents a halogen atom, a nitro group or a lower alkoxy group, $R^{3''}$ represents a hydrogen atom or a lower alkoxy group, $R^{4''}$ represents a lower alkyl group, a phenyl(lower)alkyl group or a lower alkenyl group, and $R^{7''}$ represents a lower alkoxy group.

5. A therapeutic composition for hyperlipidemia, which comprises a pharmacologically effective amount of the phosphonic ester derivative defined in one of claims 1–4 and a pharmaceutically acceptable carrier.

6. A therapeutic or preventive composition for hyperlipidemia according to claim 5 wherein the active ingredient is a phosphonic ester derivative as defined in claim 4.

7. A phosphonic ester derivative according to claim 3, wherein $R^{2''}$ represents a hydrogen atom or a lower alkyl group, $R^{3''}$ represents a hydrogen atom, a halogen-substituted lower alkyl group or a halogen atom, $R^{4''}$ represents a lower alkyl group, a phenyl(lower)alkyl group, a lower alkynyl group or a pyridylmethylideneamino group.

8. A phosphonic ester derivative according to claim 7, wherein $R^{2''}$ represents a hydrogen atom and $R^{3''}$ represents a hydrogen atom or a halogen atom.

9. A phosphonic ester derivative according to claim 8, wherein $R^{1''}$ represents a hydrogen atom, $R^{3''}$ represents a halogen atom, and $R^{7''}$ represents a lower alkoxy group or a phenyl(lower)alkylamino group.

10. A phosphonic ester derivative according to claim 9 which is selected from the group consisting of diethyl 4-(7-chloro-3-methyl-4(3H)-quinazolinon-2-yl)benzylphosphonate, diethyl 4-(7-bromo-3-methyl-4(3H)-quinazolinon-2-yl)benzylphosphonate and ethyl [4-(7-chloro-3-methyl-4(3H)-quinazolinon-2-yl)benzyl]-N-benzylamidophosponate.

11. A phosphonic ester derivative according to claim 10 which is diethyl 4-(7-chloro-3-methyl-4(3H)-quinazolinon-2-yl)benzylphosphonate.

12. A therapeutic composition for diabetes, which comprises a pharmacologically effective amount of the phosphonic ester derivative defined in one of claims 1-3 and 7-11, and a pharmaceutically acceptable carrier.

13. A therapeutic composition for diabetes according to claim 12 wherein the active ingredient is a phosphonic ester derivative as defined in one of claims 7-11.

14. A therapeutic composition for diabetes according to claim 13 wherein the active ingredient is a phosphonic ester derivative as defined in claim 10.

15. A therapeutic composition for diabetes according to claim 14 wherein the active ingredient is a phosphonic ester derivative as defined in claim 11.

16. A method for treating hyperlipidemia, which comprises administering to a patient a pharmacologically effective amount of the phosphonic ester derivative defined in claim 1.

17. A method for treating diabetes, which comprises administering to a patient a pharmacologically effective amount of the phosphonic ester derivative defined in claim 1.

* * * * *